United States Patent
Goldstein

(10) Patent No.: US 11,264,129 B2
(45) Date of Patent: Mar. 1, 2022

(54) SELECTION AND DISTRIBUTION OF DIETARY SUPPLEMENT PRODUCTS BASED ON DNA TESTING

(71) Applicant: Xygenyx Inc., Pleasant Hill, CA (US)

(72) Inventor: Alexy Goldstein, LaFayette, CA (US)

(73) Assignee: XYGENYX INC., Pleasant Hill, CA (US)

( * ) Notice: Subject to any disclaimer, the term of this patent is extended or adjusted under 35 U.S.C. 154(b) by 0 days.

(21) Appl. No.: 17/368,787

(22) Filed: Jul. 6, 2021

(65) Prior Publication Data

US 2021/0327569 A1    Oct. 21, 2021

Related U.S. Application Data

(63) Continuation-in-part of application No. 17/240,499, filed on Apr. 26, 2021, which is a continuation of
(Continued)

(51) Int. Cl.
| | |
|---|---|
| *G06F 17/00* | (2019.01) |
| *G16H 40/20* | (2018.01) |
| *G16H 20/60* | (2018.01) |
| *G16H 10/60* | (2018.01) |
| *G06Q 10/08* | (2012.01) |

(Continued)

(52) U.S. Cl.
CPC .......... *G16H 40/20* (2018.01); *G06Q 10/087* (2013.01); *G06Q 20/085* (2013.01); *G06Q 30/0201* (2013.01); *G06Q 30/0631* (2013.01); *G16B 20/00* (2019.02); *G16H 10/40* (2018.01);
(Continued)

(58) Field of Classification Search
CPC ........ G16H 40/20; G16H 20/60; G16H 10/40; G16H 50/20; G16H 10/60; G06Q 30/0201; G06Q 20/085; G06Q 30/0631; G06Q 10/087; G16B 20/00
See application file for complete search history.

(56) References Cited

U.S. PATENT DOCUMENTS 10,950,354 B1 * 3/2021 Belgoroski ............ G16H 40/20
2006/0062859 A1  3/2006 Blum et al.
(Continued)

*Primary Examiner* — Tuyen K Vo
(74) *Attorney, Agent, or Firm* — Galvin Patent Law LLC; Brian R. Galvin

(57) ABSTRACT

A system and method for selection and distribution of dietary and nutritional supplements which provides a systematic means for consumers to obtain genetic testing, receive accurate and useful information about dietary and nutritional supplements that may be of benefit to genetically-related conditions identified by the genetic testing, and to conveniently and efficiently order and receive appropriate dietary and nutritional supplements consistent with the information. The system and method involve establishing a hybrid network of traditional and non-traditional distribution points, distribution of genetic testing kits throughout the network, obtaining DNA samples at the distribution points, transmission of the DNA samples to a lab to obtain a genetic profile, analysis of the genetic profile against a supplementation database, selection of dietary and nutritional supplements appropriate for health conditions associated with the genetic profile, and delivery of the dietary and nutritional supplements to the distribution points for sale to the consumer.

4 Claims, 13 Drawing Sheets

Related U.S. Application Data application No. 17/177,122, filed on Feb. 16, 2021, which is a continuation of application No. 17/113,854, filed on Dec. 7, 2020, now abandoned.

(60) Provisional application No. 62/944,322, filed on Dec. 5, 2019.

(51) Int. Cl.
*G16B 20/00* (2019.01)
*G16H 50/20* (2018.01)
*G06Q 30/06* (2012.01)
*G06Q 20/08* (2012.01)
*G06Q 30/02* (2012.01)
*G16H 10/40* (2018.01)

(52) U.S. Cl.
CPC ............ *G16H 10/60* (2018.01); *G16H 20/60* (2018.01); *G16H 50/20* (2018.01)

(56) References Cited

U.S. PATENT DOCUMENTS

| | | | |
|---|---|---|---|
| 2015/0120633 A1* | 4/2015 | Norlander | G16H 20/70 706/46 |
| 2017/0039884 A1* | 2/2017 | Shu | G09B 19/0092 |
| 2017/0323057 A1* | 11/2017 | Karvela | G16H 10/65 |
| 2018/0218434 A1 | 8/2018 | Smith et al. | |
| 2018/0374567 A1* | 12/2018 | Toumazou | G16H 10/60 |

* cited by examiner

SELECTION AND DISTRIBUTION OF DIETARY SUPPLEMENT PRODUCTS BASED ON DNA TESTING

CROSS REFERENCE TO RELATED APPLICATIONS

Priority is claimed in the application data sheet to the following patents or patent applications, the entire written description of each of which is expressly incorporated herein by reference in its entirety.
Ser. No. 17/240,499
Ser. No. 17/177,122
Ser. No. 17/113,854
62/944,322

BACKGROUND

Field of the Art

The disclosure relates to the field of dietary supplements, and more particularly to the selection and distribution of dietary supplements based on DNA testing results.

Discussion of the State of the Art

Dietary and nutritional supplements are widely available to consumers. However, due to the lack of regulation of such supplements, consumers are left to their own devices regarding decisions on nutritional supplements. While consumers may be able to obtain some useful decision-making information based on general health knowledge, not only is accurate and well-documented information difficult to find, the consumer generally has little information about the impact such supplements may have on the consumer's own particular health conditions, particularly those which may be genetically influenced. Further, there is no systematic means of testing for genetically-influenced conditions in consumers, providing consumers with appropriate supplement-related information associated with such genetically-influenced conditions, or efficient distribution of supplements that may be beneficially to such genetically-influenced conditions.

What is needed is a systematic means for consumers to obtain genetic testing, receive accurate and useful information about dietary and nutritional supplements that may be of benefit to genetically-related conditions identified by the genetic testing, and to conveniently and efficiently order and receive appropriate dietary and nutritional supplements consistent with the information.

SUMMARY

Accordingly, the inventors have conceived and reduced to practice a system and method for selection and distribution of dietary and nutritional supplements which provides a systematic means for consumers to obtain genetic testing, receive accurate and useful information about dietary and nutritional supplements that may be of benefit to genetically-related conditions identified by the genetic testing, and to conveniently and efficiently order and receive appropriate dietary and nutritional supplements consistent with the information. The system and method involve establishing a hybrid network of traditional and non-traditional distribution points, distribution of genetic testing kits throughout the network, obtaining DNA samples at the distribution points, transmission of the DNA samples to a lab to obtain a genetic profile, analysis of the genetic profile against a supplementation database, selection of dietary and nutritional supplements appropriate for health conditions associated with the genetic profile, and delivery of the dietary and nutritional supplements to the distribution points for sale to the consumer.

According to a preferred embodiment, a system for selection and distribution of dietary supplements based on genetic testing is disclosed, comprising: a network-connected computer server comprising a memory, a processor, and a non-volatile data storage device; a business management database stored on the non-volatile data storage device, the business management database comprising: seller data comprising a seller identification for each seller and inventories of products available from each seller; product data comprising information about amounts of dietary supplements contained in a plurality of dietary supplement products; and client data comprising client names, ages, weights, and health conditions; a seller portal comprising a first plurality of programming instructions stored in the memory which, when operating on the processor, causes the processor to: receive seller data from a plurality of sellers; and store the seller data in a business management database on the non-volatile data storage device; a client portal comprising a second plurality of programming instructions stored in the memory which, when operating on the processor, causes the processor to: receive client data for a first client comprising the client's name, age, weight, and a health condition; receive a request for selection and distribution of dietary supplements that may be beneficial to the health condition; receive a genetic profile from the client, the genetic profile comprising the results of a deoxyribonucleic acid (DNA) test for the client; and store the client data and genetic profile in the business management database; a machine learning algorithm comprising a third plurality of programming instructions stored in the memory which, when operating on the processor, causes the processor to: receive the genetic profile; retrieve the first client's data and genetic profile from the business management database; and identify a dietary supplement known or suspected to be beneficial to the health condition; determine an amount of the dietary supplement based on the client's age and weight; an inventory manager comprising a fourth plurality of programming instructions stored in the memory which, when operating on the processor, causes the processor to: receive the identification and amount of the dietary supplement; identify products from the business management database containing the dietary supplement in at least the amount; determine availability of the identified products from the inventories of the sellers in the business management database; send a recommendation to the client through the client portal to purchase the identified products; receive a purchase order for the identified products from the client through the client portal, the purchase order containing a purchase price; and distribute the identified products to the client.

According to a preferred embodiment, a method for selection and distribution of dietary supplements based on genetic testing is disclosed, comprising the steps of: receiving seller data from a plurality of sellers, the seller data comprising a seller identification for each seller and inventories of products available from each seller; receiving product data comprising information about amounts of dietary supplements contained in a plurality of dietary supplement products; receiving client data comprising client names, ages, weights, and health conditions; storing the seller data, product data, and client data in a business management database on a non-volatile data storage device of a computing device comprising a memory, a processor, and the non-volatile data storage device; receiving client data for a first client comprising the first client's name, age, weight, and a health condition; receiving a request for selection and distribution of dietary supplements that may be beneficial to the health condition; receiving a genetic profile from the client, the genetic profile comprising the results of a deoxyribonucleic acid (DNA) test for the client; and storing the first client's data and genetic profile in the business management database; retrieving the first client's data and genetic profile from the business management database; and identifying, using a machine learning algorithm operating on the computing device, a dietary supplement known or suspected to be beneficial to the health condition; determining, using the machine learning algorithm, an amount of the dietary supplement based on the client's age and weight; identifying, using an inventory manager operating on the computing device, products from the business management database containing the dietary supplement in at least the amount; determining availability of the identified products from the inventories of the sellers in the business management database, using the inventory manager; sending a recommendation to the client through a client portal operating on the computing device to purchase the identified products; receiving a purchase order for the identified products from the client through the client portal, the purchase order containing a purchase price; and distributing the identified products to the client.

According to an aspect of an embodiment, the seller data of the business management database further comprises hierarchical relationships between sellers, associations of customers with sellers, and commission information based on the hierarchical relationships, and a compensation allocator is used to: determine, using a compensation allocator operating on the computing device, a first seller with which the customer is associated from the business management database; determine, using the compensation allocator, a hierarchical relationship with one or more second sellers based on the hierarchical relationships between sellers in the business management database, the hierarchical relationship comprising a degree of relationship between the first seller and each of the second sellers; and allocate, using the compensation allocator, a portion of the purchase price as a commission to each of the second sellers depending on the degree of relation of each second seller to the first seller.

BRIEF DESCRIPTION OF THE DRAWING FIGURES

DETAILED DESCRIPTION

Figure 1:
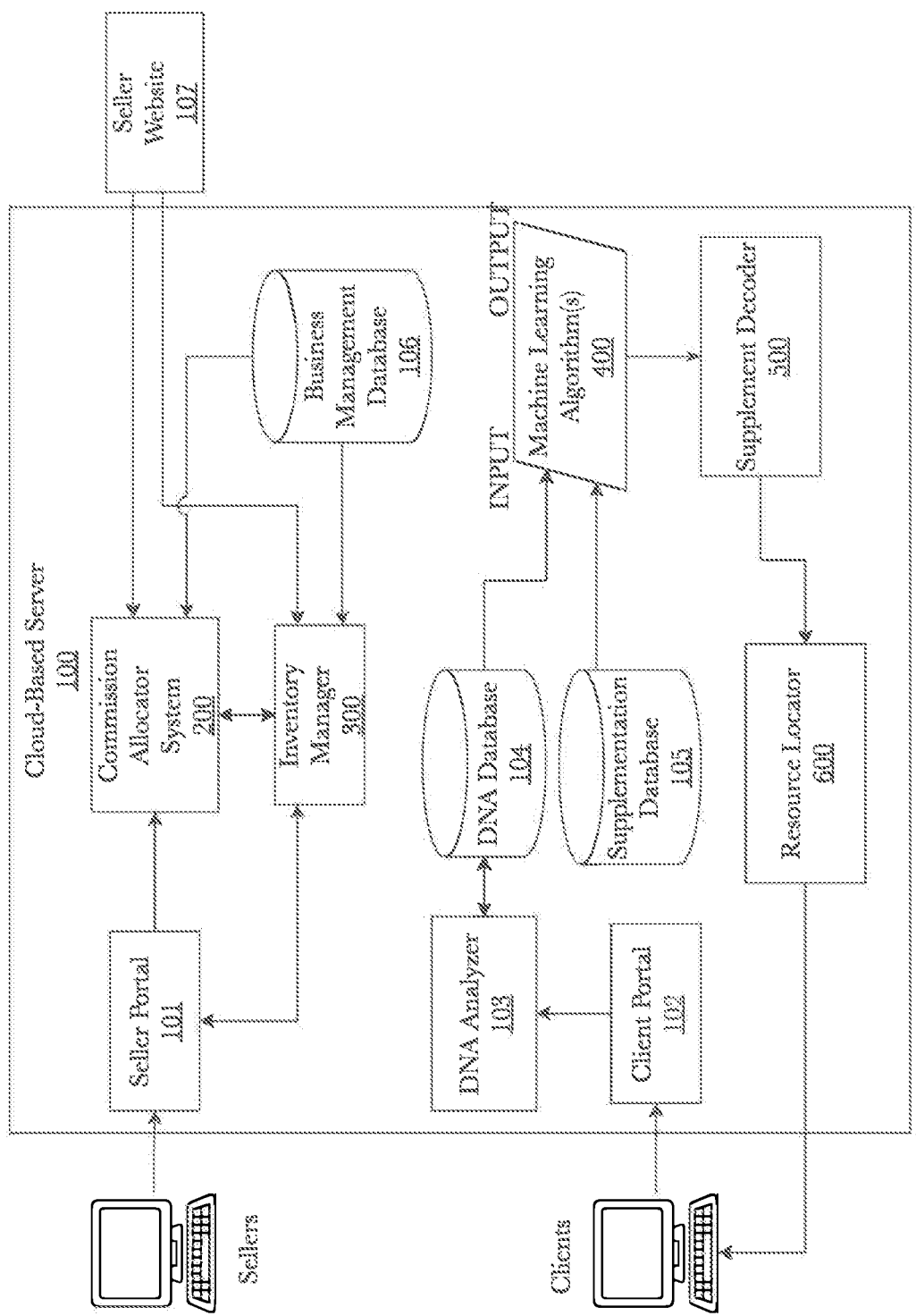
FIG. 1 is a diagram showing an exemplary system architecture for a system for selection and distribution of dietary supplements.

The inventors have conceived, and reduced to practice, a system and method for selection and distribution of dietary and nutritional supplements which provides a systematic means for consumers to obtain genetic testing, receive accurate and useful information about dietary and nutritional supplements that may be of benefit to genetically-related conditions identified by the genetic testing, and to conveniently and efficiently order and receive appropriate dietary and nutritional supplements consistent with the information. The system and method involve establishing a hybrid network of traditional and non-traditional distribution points, distribution of genetic testing kits throughout the network, obtaining DNA samples at the distribution points, transmission of the DNA samples to a lab to obtain a genetic profile, analysis of the genetic profile against a supplementation database, selection of dietary and nutritional supplements appropriate for health conditions associated with the genetic profile, and delivery of the dietary and nutritional supplements to the distribution points for sale to the consumer.

In some embodiments, the system and method involve a hybrid retail and network marketing model which allows for selling and distributing dietary supplement products amongst members contained in a multi-level marketing network. Businesses participating in the multi-level marketing network may receive benefits for expanding their network, which includes greater stock availability through distribution from its upstream(s) as well as commissions from sold supplements from downstream sellers recruited into the network by the upstream business. Another benefit of such a marketing system is a maintained stock inventory, meaning a business contained in the network marketing system does not need to order product ahead of time to account for a lack of product at the point of sale by having access to distribution from upstream sellers, which is a functionality that extends all the way to the top of said multi-level marketing hierarchy. Dietary supplements sold on the network of markets are issued by receiving a consumer's dietary supplementation requirements based on the consumer's genetic profile and issuing a list of supplementation components or proprietary supplements. Algorithms are used by the network system to discover potential new recruits for individual business owners as well as for optimizing supplementation recommendations to the consumers.

Network marketing, or multi-level marketing (MLM) has been a major channel for sales to consumers for the last sixty years at least. Independent business owners (IBOs), working from their homes and using parties, seminars, one-on-one contacts, and the like, sell products directly to consumers and recruit others to join their network. After recruiting a consumer, that consumer then becomes an IBO in her own right and is known as part of the "downstream" of the recruiting IBO. In this way, multi-level networks of IBOs are developed, extending the reach of a product's sales to large numbers of prospective buyers. A key part of the economics of network marketing sales models is that commissions generated by the sales of products (or services) are paid to some number of "upstream" distributors (IBOs who have recruited others). An attractive aspect of the network marketing approach to sales is the rapid scalability of sales of popular products.

However, some shortcomings of network marketing are apparent from the nature of the model. Unlike in traditional retail, there is no—or very limited—opportunity for merchandising of products. Moreover, established retailers generally are not able to carry products manufactured by companies that use network marketing, and so consumers may be unable to find products they want without finding a nearby IBO. And retailers are denied the opportunity to carry precisely the mix of products they feel will be most attractive to their customer base, as large numbers of products are not available to them for resale.

According to an aspect, a hybrid sales model is disclosed that combines strengths of each of conventional retail (stores) and network marketing (direct sales by independent business owners—IBOs, who are also referred to commonly as distributors) sales channels. In an aspect, a conventional retailer or merchant may desire to carry products that are sold only through a network marketing sales system. Today, such a merchant would simply not have that option, as network marketing companies are set up to protect their principal sales channel—IBOs—and therefore limit sales to those made by those IBOs. For instance, it is common for network marketing companies to provide personalized websites for its IBOs so that the IBOs can sell online directly (more or less successfully, depending on the skill and effort of each respective IBO), rather than selling directly from a company website (which would cannibalize the IBO sales opportunities, and would therefore likely result in rapid desertion by the best IBOs to "greener pastures"). According to the aspect, the merchant desiring to offer products from a network marketer is provided a path to become an IBO in her own right, effectively joining the network of the network marketer.

Joining a network marketing system may be done by converting the store to an exclusive sales channel for the network marketing system (selling only its products), which would of course represent a fundamental change in the business model of the store. Alternatively, in some aspects, the merchant may join the network marketing system and sell its products in her store alongside products she previously sold; effectively in this case the network marketer becomes a new brand and product line to be sold by the store. In either case, when a merchant joins a network marketing system, she will typically be required to attend one or more training sessions, at which time she may be assigned an existing IBO as her "upstream" (the first link in the chain of commissions upstream—when the merchant sells a product from the network marketer, she takes a portion of the commission generated by the sale, and then successively smaller portions of the remaining commission is disbursed to one or more upstream IBOs). In some cases, the selection of an upstream for a new merchant IBO may be made based on a variety of factors. For example, there may be specialist merchant recruiters who are trained to, and actively do, recruit merchants to join a network marketing system. Such merchant specialists would typically be the upstream for any merchants recruited. Or, there may be competitive assignment of merchants to upstream sellers based on sales performance of IBOs eligible to be the upstream for a new merchant. Eligibility in turn may be based on products to be sold by the merchant, the merchant's location, or even machine learning algorithms that optimally develop a network by matching personality traits of recruits and potential upstream sellers. It will be appreciated by on having ordinary skill in the art that many methods of assigning newly-joined merchants to upstream sellers will be possible without departing from the scope of the invention.

In an aspect, merchants may be paid a higher commission if they join as an exclusive seller of the network marketer's product, rather than as a non-exclusive seller. Also, it may be that commissions to a merchant IBO will vary based on the merchant's sales volume and the rate of growth of the volume.

In an aspect, a merchant IBO may act as a local distribution hub for the network marketing system as well as a sales channel. Moreover, it would commonly be expected that the merchant not only sells products to customers but also recruits new IBOs. For example, a customer of a merchant IBO may inquire about joining the network, and may in fact do so. In this case, normally the merchant would be the upstream and would therefore participate in the commission stream for sales originating with the newly-recruited customer. But, since the merchant has the ability to maintain inventory, the merchant may act as a local distribution hub for her recruited IBOs and even for other previously-recruited IBOs who reside nearby. The merchant's commission may be adjusted to compensate her for this additional service to the network marketer. It can be seen that using merchants as distributors may assist in streamlining the distribution of products to direct sellers; particularly when advanced optimization algorithms are used, inventory levels can be optimized both in terms of volume but also location, minimizing delays in product delivery to buyers while also minimizing carrying costs.

In some aspects, rather than becoming traditional IBOs, merchants become franchisees of the network marketing system, with their franchises being carefully tailored to be supportive of, rather than competitive with, the businesses of traditional IBOs. For example, while becoming a franchisee, the merchant may still be part of the downstream of a selected IBO (her upstream), so that commission flows still operate in the normal network marketing way and IBOs are not cut out of the process. Moreover, in some aspects the franchisee may provide services to IBOs in her sales region, such as distribution services or additional marketing services. The merchant might operate a referral system wherein customers of the merchant, rather than being recruited by the merchant, would be referred to an appropriate potential upstream IBO upon expressing interest in participating in the network marketing system. The merchant might receive a one-time bonus for such referrals, which may or may not be contingent on the eventual success of the recruitment, and possibly may include a longer-term compensation based on the success of the newly-recruited IBO.

According to some aspects, novel data systems may be used to support the hybrid sales model described herein. For example, the recruitment process will typically involve a much higher level of indirection than traditional network marketing recruiting; merchants may go directly to the corporation to seek a franchise, and would not necessarily be recruited by any IBO, yet they have to become part of the network and must be inserted at a location that reinforces rather than compromises the perceived integrity of the network marketing system. For another example, inventory and distribution management can be improved or degraded, depending on how successfully merchants are integrated into existing supply chain systems. In some aspects, merchants may act not only as sales channels but also as distribution nodes, and advanced machine learning and optimization algorithms may be used to optimally manage distribution and inventory in this more-complex environment. Such an approach allows that maintenance of leaner inventory at the same time as it allows the inventory to be closer to the point of consumption. Similarly, the inclusion of merchants—who in principle may be capable of directly selling much more product than any single IBO—will tend to vastly complexify the distribution of commissions, and the use of artificial intelligence to optimally and equitably refine the compensation structure while incorporating merchants is expected to be common.

In a novel aspect, some merchant stores in a network marketing system may be provided with DNA testing kits (for example, saliva testing kits, although any form of DNA testing known in the art may be used according to the invention), as part of a holistic genetic supplementation offering. For example, a consumer may walk into a store of the network marketing participant merchant, obtain information on the benefits of DNA testing and genetically-guided nutritional supplementation, and provide a DNA sample. In an aspect, consumers may be provided the option to formally grant permission for the merchant (specifically, specially-trained genetic counseling employees of the merchant) to receive a copy of the DNA test results (in most aspects, DNA sequencing/testing would be done offsite after the sampled DNA is mailed to certified testing facilities; results would be provided to the consumer as well as the merchant's genetic counselor employee). The consumer would then return in two weeks to receive her DNA test results (which would be delivered to the store; the merchant would only be able to view the test results if the consumer had granted permission at the time of testing or subsequently). According to an aspect, based on the DNA test results for the specific consumer, the consumer may be identified with a specific known genetic nutritional profile (as a very simple example, a consumer having a known SNP—single nucleotide polymorphism—variant in the ORIOA2 gene would have an aversion to cilantro). Such nutritional profiling based on discrete DNA tests is known in the art, but most of the profiling is done at the single-SNP level such as the example just given—another more meaningful single-SNP example being ADIPOQ, which deals with propensity to regain weight—but it is envisioned that groups of known SNP variations may be common that may suggest specific supplementation strategies. Moreover, according to an aspect machine learning may be used to develop optimized dietary supplementation strategies that are beneficial for commonly occurring groups of genetic variants. Also, in some cases a set of known genetic variations may have common overall dietary issues that can be addressed using a single optimized formulation. In particular, according to an aspect, a plurality of specialized proprietary dietary supplement formulations are available in the merchant's store, provided by the network marketing system, so that the consumer, on receiving her genetic testing results, may be guided to the purchase of a specially-formulated supplement designed for her specific genetic nutritional profile.

According to an aspect, consumers may receive an enhanced health benefit by receiving genetic testing and tailored supplementation optimized for each consumer's specific genetic nutritional profile, all in one location. Additional genetic counseling may be provided onsite as well, and it is envisioned that the merchant venues using the invention may become a healthy alternative to the conventional drugstore of old. As new genetic variations that may affect or be ameliorated by diet and nutrition, and as machine learning identifies new clusters of genes that enable ever-more refined nutritional profiling, additional proprietary supplements are made available by the network marketing system. Of course, once a consumer has been profiled and been introduced to the optimized dietary supplement formulation specific to nutritional profile, the consumer may not only obtain his supplement products from the merchant who did the testing but also from any MO who participates in the network marketing system.

It will be appreciated that many enhancements and variations to the hybrid retail/network marketing sales system and the in-store genetic testing and supplementation services described herein are envisioned. For example, not only retail stores but also health care providers could become franchisees (exclusively or not) of the network marketing system and could provide the genetic testing and counseling and the special genetic profile-based formulations as part of their healthcare service package. Common types of healthcare providers that would be suitable for such participation include naturopaths, chiropractors, osteopaths, nutritionists, and so forth. According to another aspect, a comprehensive database of nutritional supplements and micronutrients, with their known biological and health characteristics, may be used along with data from genetic testing to automatically identify candidate formulations optimal for more and more refined genetic nutritional profiles. For example, someone with problematic SNP variants in the TCF7L2 (sugar sensitivity), SLC2A2 (sweet tooth), DRD2 (food reward), and FAAH (happiness) might be provided with a formulation designed to elevate mood and reduce appetite, and that would tend to reduce the desire to eat sweets (in a similar way that a common pharmaceutical treatment for alcoholism is to administer a drug that makes alcohol consumption lead to nausea). It will be appreciated that such a tailored formulation would work well with many similar genetic profiles, but in general it is expected that as ongoing machine learning progresses the number of distinct formulations targeting non-trivial genetic profile groups will continue to grow, as refinements occur to differentiate between similar profiles. Moreover, in some aspects software may be used in service delivery locations such as the stores or healthcare providers discussed herein to custom-mix a dietary supplement specifically designed for an individual genetic nutrition profile; such a formulation could also be adjusted to account for stated preferences of modality/form factor, flavor, method and timing of administration, and so forth. Such "compounding supplementation" could start with existing proprietary formulations that cover most of a person's profile, with a few added ingredients that take into account the differences between the person's profile and the "standard" profile upon which the proprietary formulation was based. It will be seen that, over time, the use of an integrated testing, formulation, and distribution channel underlain by extensive analytics and machine learning will lead to more and more personalized dietary supplementation.

According to various aspects, and as non-limiting examples only, one or more of the following genes may be used to generate nutritional profile-specific supplement formulations:

APOE—Age-related metabolism
FABP2—Fat-processing ability
APOE—Fatty acid sensitivity
PPAR—Monounsaturated fat
TCF7L2—Sugar sensitivity
TRHR—Lean body mass
CDR—Muscle Mass
GDF5—Joint Workout Response
COL5a1—Flexibility
VEGF—Aerobic fitness
ACE—Endurance
ADRB3—Energy Output
ADRB2—Muscle Function
BDKRB2—Muscle Efficiency
ADRB2—VO2 Max
EDN1—Training Response
ACTN3—Muscle Force
AGT—Muscle Power
MSTN—Strength Building
ALDH2—Alcohol breakdown
TAS2R38, parts 1, 2, and 3—Bitter taste
ORIOA2—Cilantro aversion
CYP1A2—Caffeine metabolism
FADS1—Fatty Acid Breakdown
PPARG—Monounsaturated fat
LEPR—Appetite
DRD2—Food Reward
FTO—Feeling Full
NMB—Hunger
MC4R—Weight Gain
SLC2A2—Sweet tooth
ADIPOQ—Weight regain
BCM01—Beta Carotene (Vit. A)
NBPF3—Vit. B6
FUT2—Vit. B12
SLC23A1—Vit. C
GC—Vit. D
OCTR—Empathy
OPRM1—Euphoria
FAAH—Happiness
SLC6A2—Positive Mood
CLOCK—Agreeable mood
ADORA2A—Caffeine Response
DRD2—Food Reward
DRD4—Risk Behavior
GCH1, SCN9A—Pain Tolerance
COMT—Warrior or Worrier
C11orf49—Complexion
IRF4—Hair Graying
PAX3—Monobrow
AQP3—Skin Hydration
EDAR—Thick Hair
GPX1—Antioxidant enzymes
STXBP5L—Photo aging
CATALA—Sun-induced aging
NQO1—Skin Renewal
AGER—Sugar-induced aging
H1F1A—Cellulite
MMP1—Collagen Breakdown
MMP3—Skin Wrinkling
FN1—Stretch Marks
MC1R—Sunlight Response
ASIP—Suntan FIG. 1 is diagram showing an exemplary system architecture for a system for selection and distribution of dietary supplements. Sellers and clients interact with the system through a seller portal 101 and a client portal 102, respectively, both of are part of a cloud-based network system 100. Connections to the seller portal 101 and client portal 102 may be made through any form of network connection including, but not limited to: Internet, Local Area Network (LAN), Wide Array Network (WAN). These portals 101, 102 may contain application programming interfaces (APIs) for the cloud-based network that allow execution of functions which operate on data contained in the cloud directly on the seller websites 107, of which said functions may perform read/write operations with data contained on a cloud-based network. The cloud-based network is also accessible by downstream sellers which have been recruited by an upstream seller, whereby each business is given a unique form of identification upon entering said network such as an ID or token as well as some form of reference to (e.g., a linked list, array, tree, or other such means) to the upstream seller. Said references can be utilized for allocating commission and other methods pertaining to the hierarchy of businesses which will be described herein. A business node database 106 contains information for each unique node contained in the network, said information may include: upstream association, downstream associations, location, stock information, and questionnaire response information. Said questionnaire may be requested by the joining business upon entering said network and be utilized for determining potential upstream/downstream associations.

The system further comprises a commission allocation system 200 and an inventory manager 300, which operate on data pertaining to each individual business on the network as it relates to their inventories and distributions to upstream and downstream sellers. The information from the inventory manager 300 may be used as an input for an algorithm, which is persistently fed newly acquired data to the network, via public databases off the network or a database contained on the network. A DNA analyzer 103 is used for obtaining consumer test results and sending the data into a DNA database 104. A supplementation database 105 comprises proprietary supplementation information, dietary components for supplementation, and known or suspected biological effects, especially including known or suspected biological effects associated with genetic markers and conditions associated with genetic markers.

This information may also be fed into one or more machine learning algorithms 400, which use the genetic profiling information of consumes and the information in the supplementation databased to determine an optimal composition/supplement profile for a given consumer based on his or her genetic profile results from the DNA analyzer.

A supplement decoder 500 identifies products available on the market containing amounts of the dietary supplements determined by the machine learning algorithm 400 to be of benefit and selects certain products and/or brands of products that contain at least the amounts determined. The selection made by the supplement decoder 500 may include individual products or combinations of products. In some cases, the supplement decoder 500 health conditions may produce a list of proprietary supplements containing said components or a custom-made mixture of products for preparation at a business on the network capable of mixing or combining certain products. In some embodiments, the supplement decoder 500 may be a part of the inventory manager 300, or some of the functions of the supplement decoder 500 may be performed by the inventory manager 300.

A resource locator 600 receives data from the decoder 500 and may utilize stock information of nodes contained in the network from the business node database 106 to determine the best available access point for obtaining the products or combinations of products identified by the supplement decoder 500. In some embodiments, such products may be from the direct upstream to the seller or an upstream higher in the hierarchy. In some embodiments, the resource locator 600 may be a part of the inventory manager 300, or some of the functions of the resource locator 600 may be performed by the inventory manager 300.

The machine learning algorithm 400 is trained to make selections based on supplementation data health conditions contained in the supplementation database, which may include proprietary supplementation information, publicly-available supplementation information, dietary components for supplementation, and known or suspected biological effects, especially including known or suspected biological effects associated with genetic markers and conditions associated with genetic markers. The machine learning algorithm 400 may be re-trained or updated based on new information provided to the supplementation database. The new information may come from a variety of sources, such as news articles, published scientific studies, reports from customers, online reviews of consumers, etc. It is known by those skilled in the art that the algorithm is expected to produce more efficient results as more data is added to the network via off-site databases as well as databases maintained on the network itself.

After the machine learning algorithm 400 has been trained on a large dataset or data sets, it may be applied to make dietary supplement selections for individual consumers. For example, if a customer's genetic profile shows that he or she has the AGT (Muscle Power) gene, the machine learning algorithm 400 can select dietary supplements known or suspected to be beneficial to health conditions associated with that genetic condition.

In an aspect, when a client connects to the seller's website 103 a connection is made to the network via client portal 102 which acts as an interface for said cloud-based network. The connecting user is met with a login verification system, which sends/receives information to the business node database 106 accessible by all authorized businesses contained in the cloud-based network. Said connection interface may utilize technology such as, but not limited to, ODBC (Open Database Connectivity), which is a database management interface allowing at least a plurality of websites to perform push/fetch/pull operations with a database contained on the network. This means a given customer only has to submit DNA to the network once and it may be accessed by all authorized upstream/downstream businesses contained in the network.

In an aspect, data contained in the supplementation database 105 may include information from public databases (such as NIH, USDA etc.). Said repositories contain label information for proprietary supplements which can be issued to the network database via a pull request. Said data may include individual components of dietary supplements, their effect(s) on usage, or any other information which may pertain to the individual supplement and be used for optimizing a mixture or profile for the consumer via the machine learning algorithm 400.

In another aspect, said genetic profile input to the machine learning algorithm 400 may be given different weight values based on the information from the consumer which may include race, age, ethnicity or other characteristics which can have an effect on propensities/health conditions as it relates to genetic profiles or conditions associated with genetic profiles. For example, if a genetic profile indicates that a given consumer might be susceptible to age-related hearing loss, the consumer's age would be relevant input data to the machine learning algorithm 400, as different dietary supplements or different amounts of dietary supplements may be recommended.

As it relates to business locations and stock availability, an increase of businesses locations on the network will enhance the availability of respective supplements to the consumer. In order to promote the expansion of said network the commission allocation system 200 allows for compensation opportunities for upstream businesses on the transactions carried out by recruited members. According to an embodiment, the upstream business may receive a certain percentage of commission based on factors which may include: an agreement made between the businesses, success factors of the downstream business (selling rates, duration the business has been in the network) or their respective position on the hierarchy of recruited businesses. For example, the commission may propagate upward from the selling business with each respective upstream getting a certain percentage based on their position in the hierarchy.

In an aspect, data pertaining to businesses on the network will have information relating to their respective inventories and locations stored in the business node database 106. Said information may include stock information, supplements sold by the business most frequently, demographic information of their consumers and references or links to their upstream/downstream businesses. The combination of business stock and transaction information along with consumer data associated with the respective businesses may be used by the resource locator 600 for optimized distribution of said dietary supplementation distribution to the consumer by determining which stock to distribute from the upstream prior to when it is requested.

In another aspect, the business node database 106 may contain questionnaire information which is requested by the joining business upon entering the network. In some embodiments, contents of the survey may include personal or social information such as personality type, gender, race, age etc. and other traits for the seller. This information may be used as a component for determining the best available upstream business for a new recruit or for finding potential downstream businesses for being recruited into the network. For example, if an upstream business which has submitted its questionnaire that it prefers to work with business owners who are outgoing, the upstream business can be recommended potential recruits which have indicated that personality trait in their respective questionnaires.

In an aspect, the resource locator 600 utilizes data from the business node database 106 which contains location and stock information for the respective businesses on the network. Said data, in combination with the results from the supplement decoder 500, may be used for determining the best available location to the consumer to pick up a supplement or have it distributed by an upstream. If the requested resource is unavailable from the upstream business, the next available upstream business will be queried by the resource locator and the process will continue upward until the hierarchy has been tapped, in which case it may be requested by the seller for distribution from another IBO on the network which is an upstream/downstream of a separate business. This is made possible by the linked-list style of functionality for the network with all participating businesses having some form of connection with each other by way of a unique token or ID.

In an aspect, supplement decoder 500 may contain a list of proprietary dietary supplements contained in the supplement database 105. These supplements may have whole or individual components which are known to aid in a certain genetic health condition.

In another aspect, supplement decoder 500 may identify individual components of dietary supplement products known for aiding genetic health conditions. Said components may be issued to the seller, or to a business contained on the network which has a means for developing a custom-mix for a supplement product in which case the individual components will be used to compose such a mixture.

Figure 2:
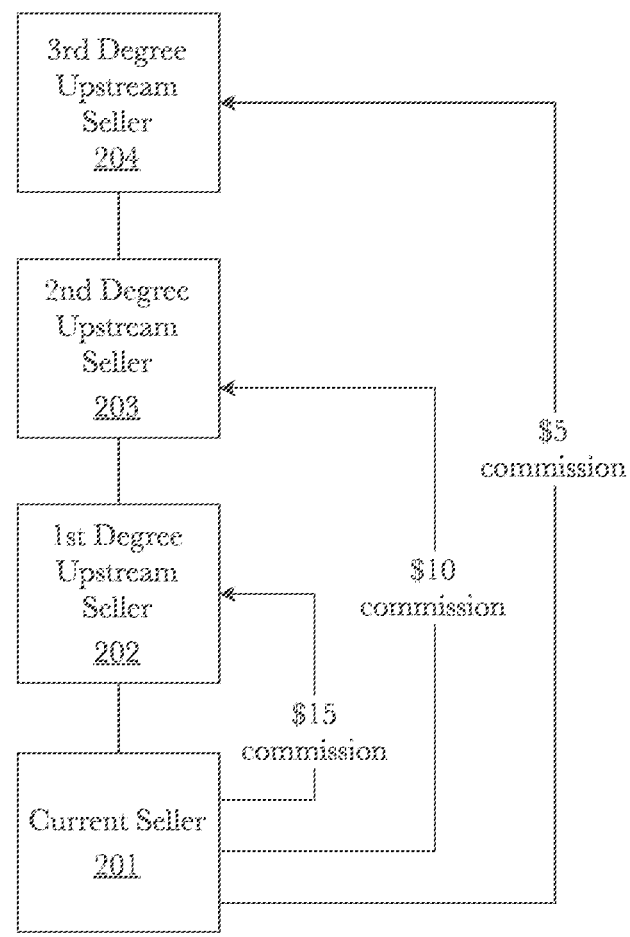
FIG. 2 is a flowchart describing an exemplary method of issuing commissions to upstream businesses from downstream businesses in the network.

FIG. 2 is a flowchart describing an exemplary method of issuing commissions to upstream businesses from downstream businesses in the network. This method may be applied as an algorithm by the commission allocation system 200. The method comprises issuing commissions to multiple upstream sellers 202-204 from a current seller 201 using the commission allocator system 200, with the amount of the commission being gradually reduced the further away the upstream sellers are from the current seller.

All upstream sellers have some form of a reference to their downstream sellers, which may be a reference ID or some other form of a unique identifier stored in a database contained on the cloud-based network. Said reference is used for determining the respective business's position on the hierarchy of the multi-level marketing system. An exemplary method for such a reference of which those skilled in the art of programming will understand, is a "Linked List", in which nodes contained in said list have a reference to a previous and next position contained in the list. However, said method is not required and may not be the only method for performing said referencing for businesses contained in the network. According to the embodiment in this figure, commission is distributed in a propagated fashion as described by propagation lines. The amount of distributed commission from completed transactions may be determined by each seller's position in the hierarchy in relation to the downstream seller. For example, if a current seller 201 makes a $100 sale, the $1^{st}$ degree upstream seller (i.e., the seller who recruited the current seller) 202 receives a $15 commission, the $2^{nd}$ degree upstream seller (i.e., the seller who recruited the $1^{st}$ degree seller) 203 receives a $10 commission, and the $3^{rd}$ degree upstream seller (i.e., the seller who recruited the $2^{nd}$ degree seller) 204 receives a $5 commission. In this way, sellers at all levels are incentivized to both recruit new sellers directly and to have those recruits continue to expand their downstream networks.

Figure 3:
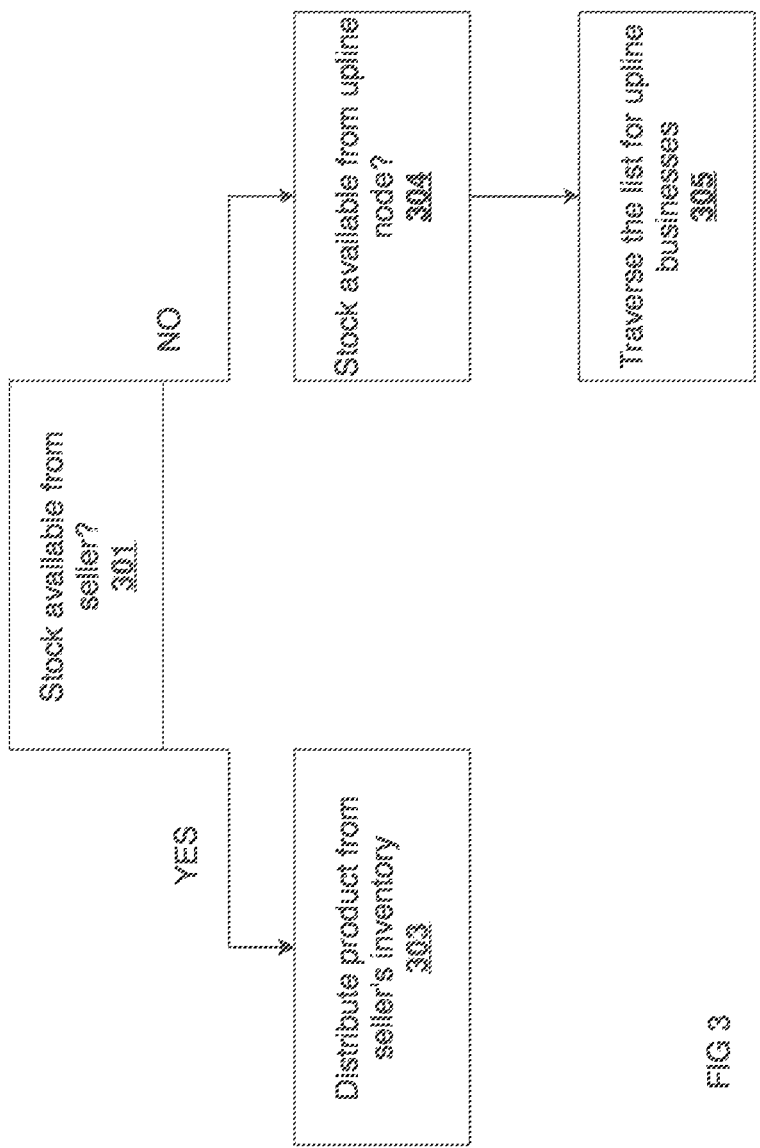
FIG. 3 is a flowchart describing the process of requesting distribution from upstream businesses on the network.

FIG. 3 is a flowchart describing the process of determining stock availability amongst the network of businesses. Stock information for the selling business is queried 301, which will return the availability for said product directly from the seller and ship the requested product 303. If the stock is unavailable, the linked-list styled connection of the network allows for traversal to the next available upstream business in the case of lack of availability whereby the upstream business has their stock information queried 302. If the immediate upstream business for the seller does not have stock available, the list will continue to be traversed 303 until the list of upstream sellers has been exhausted. Upon exhausting said list of upstream sellers the user may be prompted with a message explaining the unavailability of said product and the seller or upstream businesses associated with the seller may be notified through their respective seller portal the desire for said stock.

Figure 4:
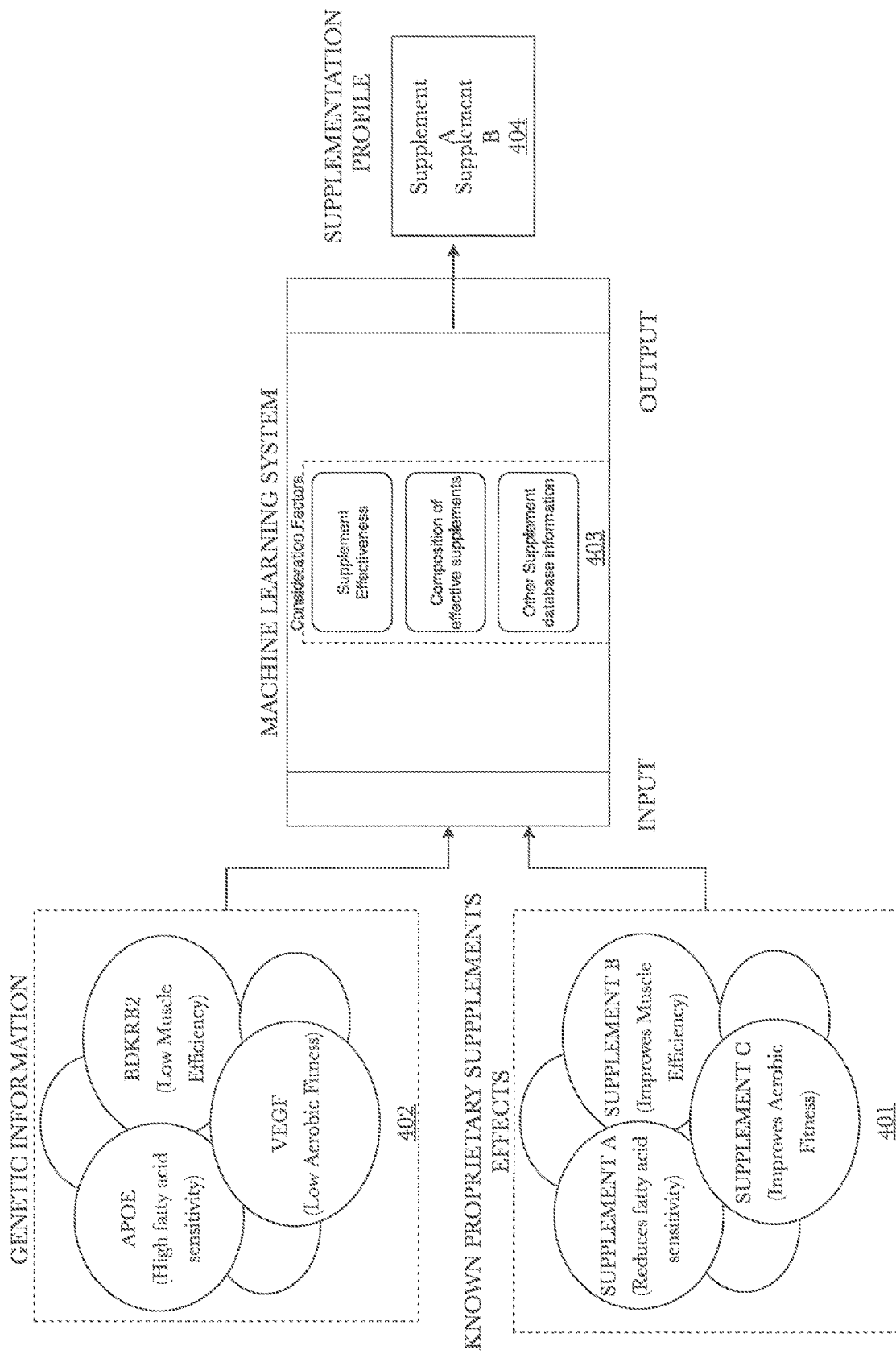
FIG. 4 is diagram showing an exemplary method for determining a supplementation profile for a consumer.

FIG. 4 is diagram showing an exemplary method for determining a supplementation profile for a consumer. Although a machine learning algorithm is used in this example, any algorithm which operates by comparing genetic information with known or suspected dietary supplement effects may be used to produce a supplementation profile through a list of consideration factors 403. Said factors, which include the effectiveness of a supplement at treating a health condition, which may be information disclosed in a supplementation database or pulled from a database of responses to the consumption or selling of a supplement such as Google reviews, Amazon reviews etc. The composition of said supplements, which may in part or whole have an effect on said health condition, as well as other possible data which pertains to supplement information pulled from database(s) and contribute to treating a health condition for one or more genetic traits. Genetic information from the consumer 402, which is contained in a database accessible by all business locations contained on the network, is fed into the algorithm as an input for seeking out the supplements or supplement components for developing supplementation profile 404 or issuing the seller a list of components for a personalized mixture. Said mixture may be comprised of multiple components which have been known to affect the health condition through information contained in publicly accessible supplementation databases 401 or reviews on websites for supplementation products. It is known by those skilled in the art of software development that such an algorithm as described herein will improve its predictive results as it pertains to an effective supplement as more data is fed into the system.

Figure 5:
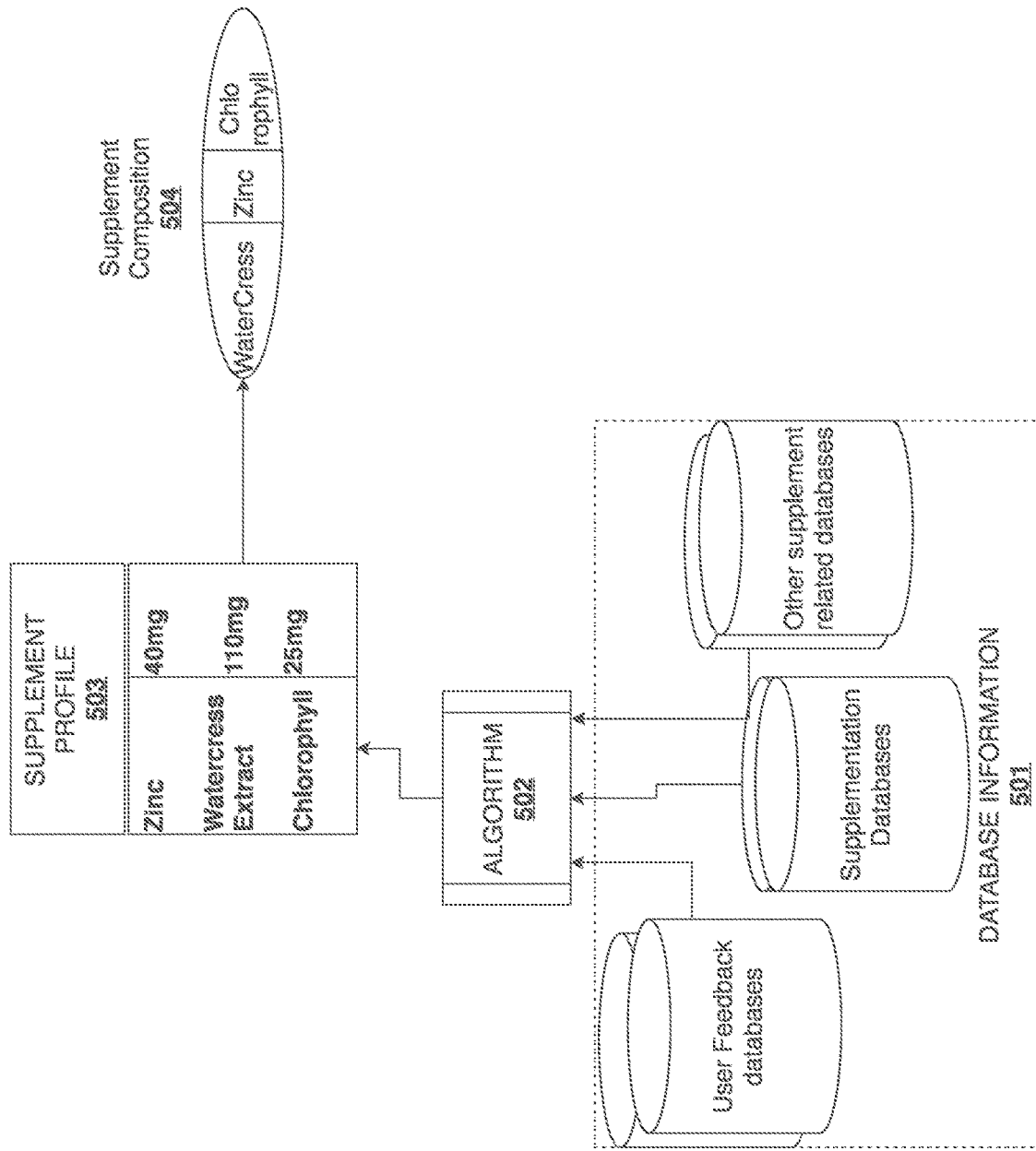
FIG. 5 is a flowchart describing the process of decoding information from an algorithm to determine supplementation recommendation(s).

FIG. 5 is a flowchart describing the process of obtaining database information 501 and issuing a supplementation product 504 based on results from algorithm 502. The algorithm may be a machine learning algorithm or another form of algorithm which accepts data and utilizes the information to enhance its decision-making capabilities. Where a machine learning algorithm is used, for example, the machine learning algorithm may be trained to determine the effective individual components for conditions associated with certain genetic profiles based on datasets obtained from such sources as online user reviews and commentary, public database information from health websites, published scientific research studies, internal customer reviews and comments, seller feedback as to customer satisfaction, and other database information which may pertain to individual components or whole proprietary supplements and give indication of a product for elevating levels of the consumer which submitted Genetic profile to the cloud-based network. As data is fed into the learning algorithm with individual components/proprietary supplements associated with a certain health condition/propensity, which are most commonly known and have effective results and may be realized in part or entirely through the individual databases 501, The produced supplementation profile 503 is the result from a supplementation decoder described herein, which initially may be a component list as is displayed in the figure and can be utilized for a mixture as is shown in 504.

According to one embodiment, the results from said algorithm may be a list of individual proprietary supplements which contain at least a plurality of ingredients which pertain to a certain health condition. The algorithm 502 may determine which of said supplements contain the most of a known ingredients for a health condition, which is expected to become more accurate and produce a more desirable result overtime as more data is fed into the system.

Figure 6:
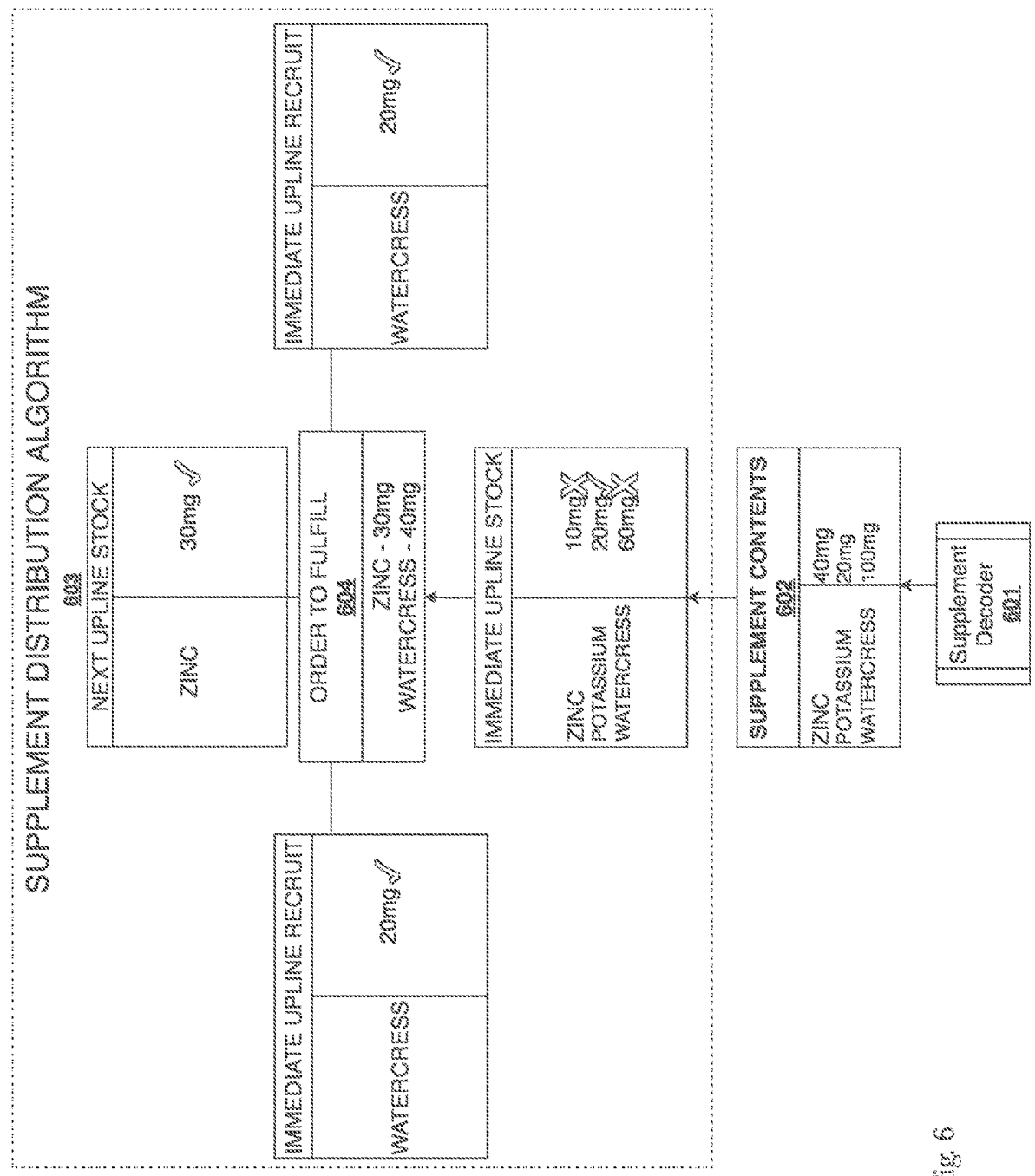
FIG. 6 is a flowchart showing an example of requesting product for distribution from businesses contained in the network based on an algorithm.

FIG. 6 is a flowchart describing a possible implementation of a supply chain algorithm for efficient sourcing and distribution of components of dietary supplements for combination into a custom mixture. Supplement decoder 601 receives output from an algorithm pertaining to the issuance of DNA supplementation based on a consumer's genetic profile and the respective health conditions of said consumer associated with the genetic profile. The supplement decoder 601 outputs a file containing specific supplementation information, which may be a text file or some form of a filetype which can be parsed to separate individual component requirements 602. According to this embodiment, the algorithm 603 checks the inventory for the immediate upstream associated with the requesting business. If said inventory does not fulfill the order 604 the algorithm checks other businesses contained on the network which will depend on the implementation. Once the contents of the order have been located, the distributor for each business is notified via its respective seller portal with a shipment request of the contents and their amounts to the downstream business.

Figure 7:
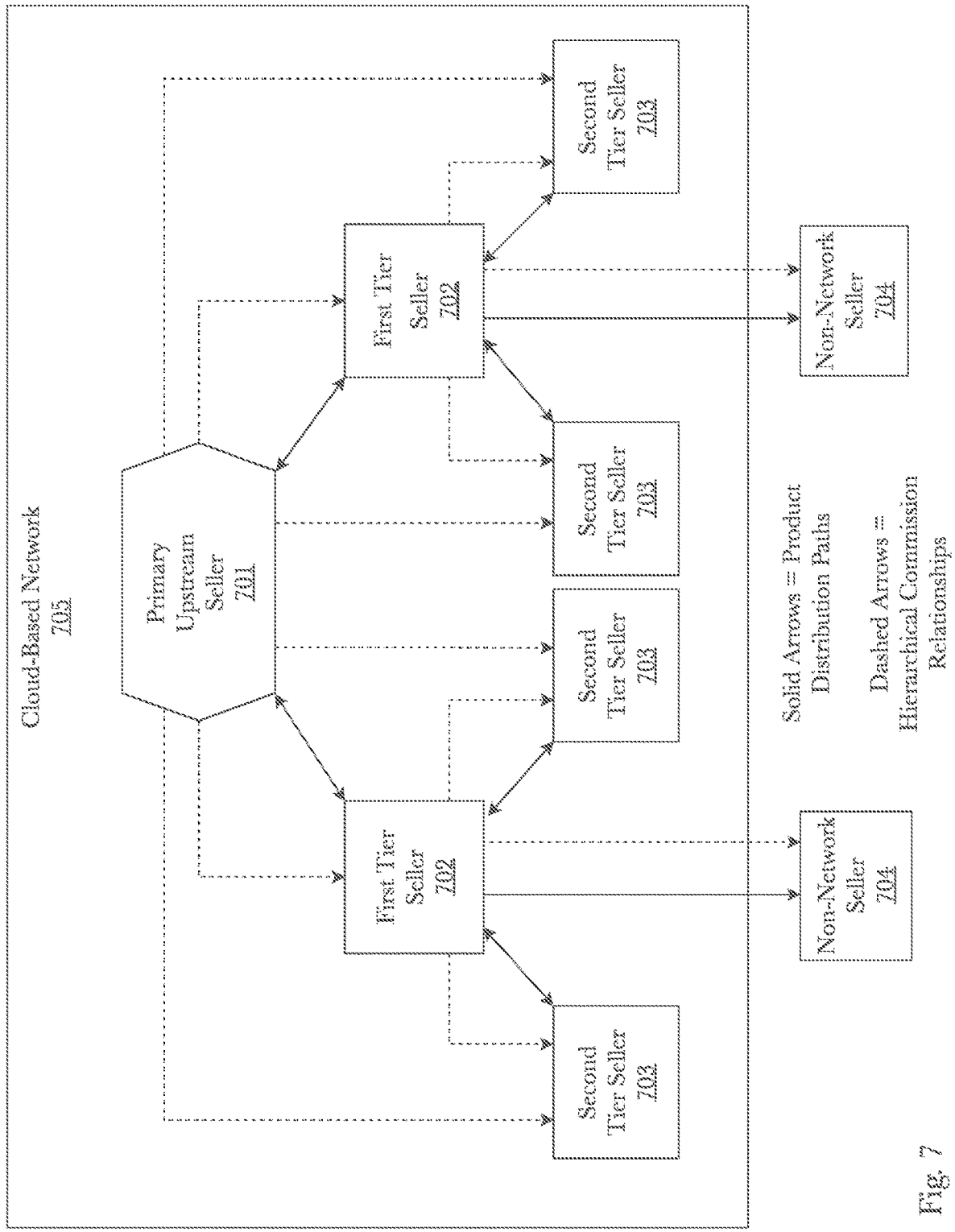
FIG. 7 is a diagram showing the congregate inventory for distributing product amongst businesses contained in a cloud-based network.

FIG. 7 displays the distribution connection between upstream sellers and their recruited downstream sellers in a multi-level marketing system. The sellers, whether upstream or downstream, may be individual sellers or independent business organizations (IBOs)). Some sellers may have their own product websites which they integrate into the cloud-based either in full or in part, receiving commissions on sales of products for which they have been recruited as sellers. In this embodiment, the primary upstream seller 701 has recruited first-tier downstream sellers to the network 702. These first-tier downstream sellers may have been issued a website from the upstream recruiter or may have integrated their existing product websites to the cloud-based network 705, as noted above. The first-tier downstream sellers 702 have recruited second-tier downstream sellers 703. The downstream sellers recruited by the upstream sellers have access to distribution of supplements from the upstream sellers at any level, in contradiction to traditional multi-level marketing schemes which enforce a strict hierarchy of distribution. Commissions, however, are still enforced in a hierarchical manner, depending on who recruited whom into the network. This results in a more efficient inventory warehousing and distribution scheme while still maintaining the hierarchy of commission payments.

According to a different embodiment, the recruited members may not have agreed to opt in to the cloud-based network system in which case they may be issued websites from their direct upstream sellers and must go through their direct upstream sellers. This methodology applies to non-network-based recruits 704, as well. If the recruited seller chooses to opt in to the network, the he or she may have access to the upstream seller's supplement inventory, which allows for a means to distribute supplements via distribution lines 704 and is a functionality accessible by all downstream sellers in the cloud-based network.

In an aspect, if a customer requests a supplement from a seller's website, the stock information contained in a database for all upstream and downstream sellers will be queried until a match is found for said the requested supplement. Once available product has been located, the product may be shipped from the business which has stock containing said product directly to the customer. The distributing seller may receive a commission for such an operation, or the commission may be paid through the hierarchical commission scheme, or both, depending on the network configuration and agreements.

In another aspect, if a seller that is franchised by a participating in-network seller makes the decision to opt out of the network, as is the case with recruits 703, their stock availability is directly tied to the upstream business and cannot query the database contained in the cloud-based network. Commissions from the transactions of said non-network-based recruits may differ compared to network-based recruits depending on the implementation.

According to another embodiment, the supplement decoder may issue a list of proprietary supplements, in which case the same procedure of checking the stock of businesses linked to said business based on an algorithm 603 remains.

Figure 8:
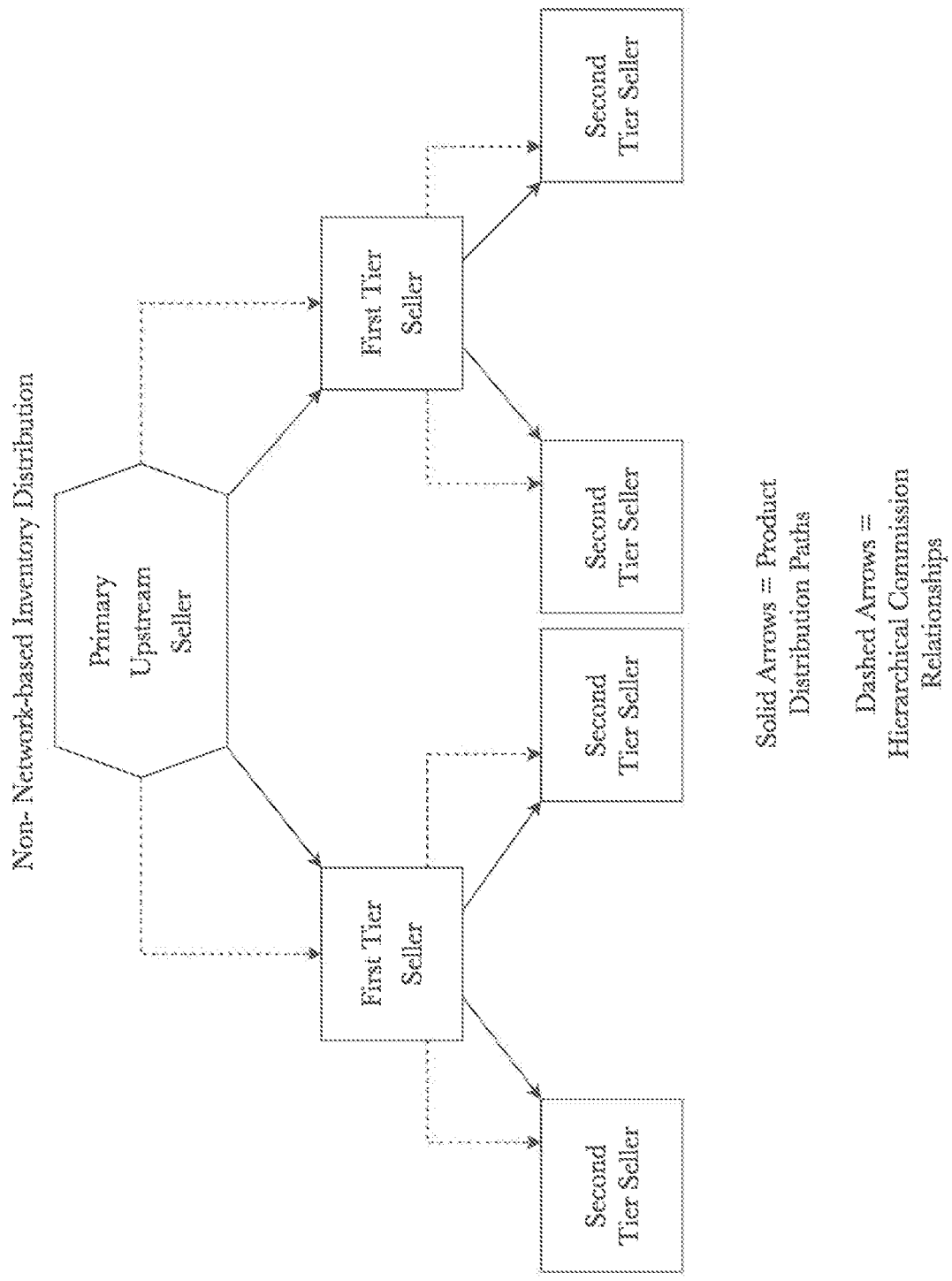
FIG. 8 (PRIOR ART) shows an example of a standard multi-level marketing system.

FIG. 8 (PRIOR ART) shows an example of a standard multi-level marketing system. Given their lack of cloud-network capabilities and linkage to upstream sellers, all recruited sellers are limited to receiving products from their direct upstream sellers. This means that product distribution is not connected to a wide network and thus their product availability is limited to those products provided by their immediate upstream sellers. Likewise, the incentives for recruiting new members to the network is stifled by lack of distribution options. A seller participating in a system such as this one may be reluctant to recruit downstream sellers due to this inventory restriction, whereas the network distribution system as described in FIG. 7 allows for the inventory to be managed throughout the network.

According to one embodiment, said commission may be dependent on the seller which is distributing the supplementation product. For example, if an upstream seller of the $3^{rd}$ degree is distributing said product to a downstream seller, the upstream seller may receive more commission for the product sold compared to sellers that are lower in the hierarchy. Said factors may be determined by an algorithm, which may contain weighted values pertaining to at least a plurality of factors, factors that may include but are not limited to: a distributing seller's position on the hierarchy, the duration said seller has been connected to the network, or even the rate of transactions for said seller.

In an aspect, a recruited seller to the multi-level marketing system may choose to opt out of the cloud-based network and become a traditional franchise which means omitting access to the distribution means described herein. In such a case, commission decisions may instead pertain to factors which are determined by the direct upstream to said business.

Figure 9:
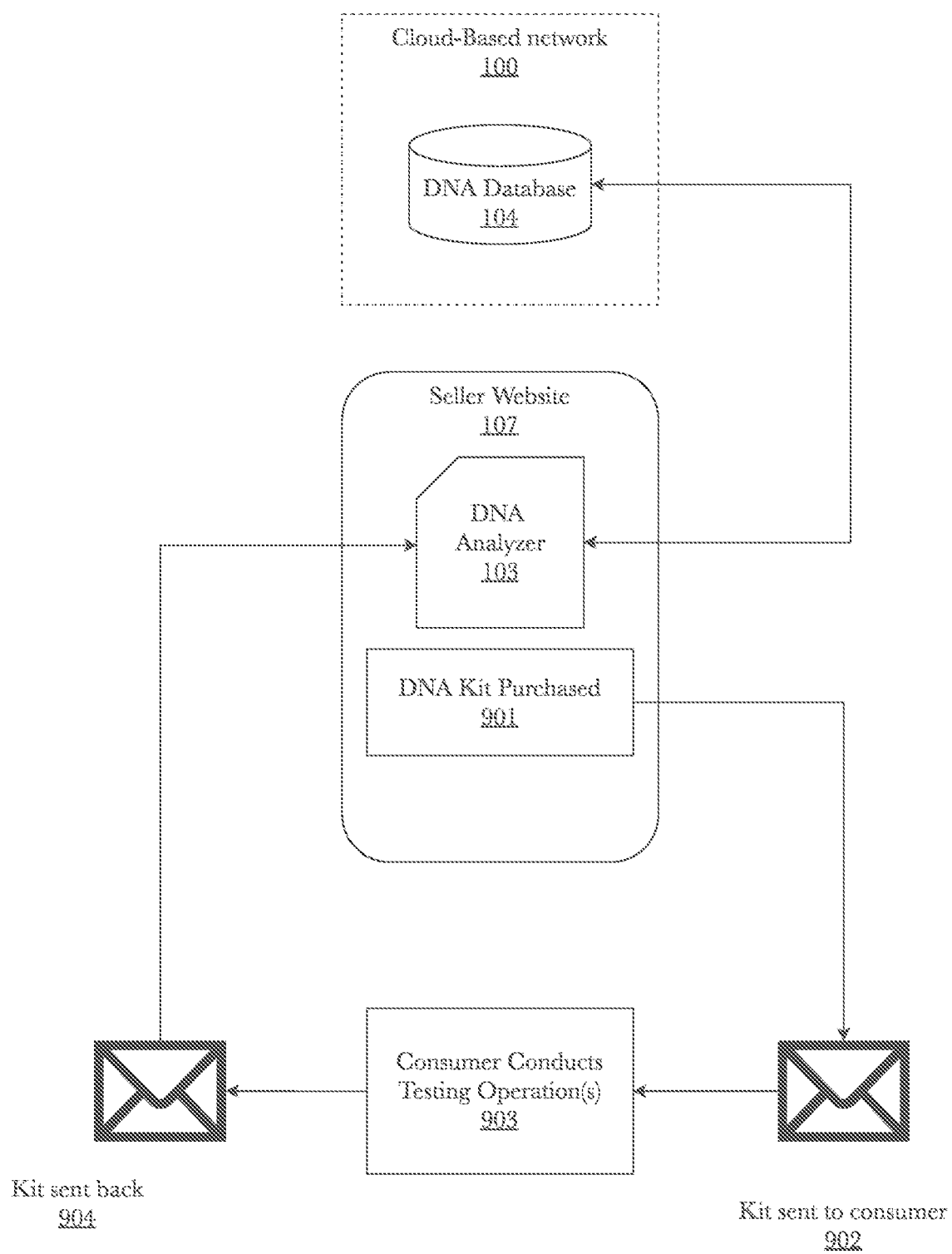
FIG. 9 is a flowchart describing an exemplary method for issuing a DNA testing kit to a consumer and submitting the results to a DNA analyzer contained on the network.

FIG. 9 is a flowchart describing an exemplary method for issuing a DNA testing kit to a consumer and submitting the results to a DNA analyzer contained on the network. In some embodiments, a customer' first interaction with a seller may be through the seller's website 107. If the customer (also known as a client) simply wishes to purchase products, the purchase may be made directly through the seller's website 107. However, if the customer wishes to get recommendations for treatment of specific health conditions, the customer may be directed to the client portal 102, wherein the customer is asked to provide certain information about himself or herself, including information such as name, age, gender, and the health condition or conditions about which the customer would like more information. Subsequently, the customer may purchase a deoxyribonucleic acid (DNA) testing kit 901, which may be sent to the customer 902, or which the customer may pick up from the seller's place of business. Upon receiving the kit 902, the customer conducts the necessary testing procedure 903 (which may involve sending a sample of the customer's DNA to a third-party genetic testing laboratory 904), resulting in the customer receiving a genetic profile. The customer then submits the genetic profile to the DNA database 104 on the cloud-based server 100 through the client portal 102. Information from said database is routed to DNA analyzer 103.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Figure 10:
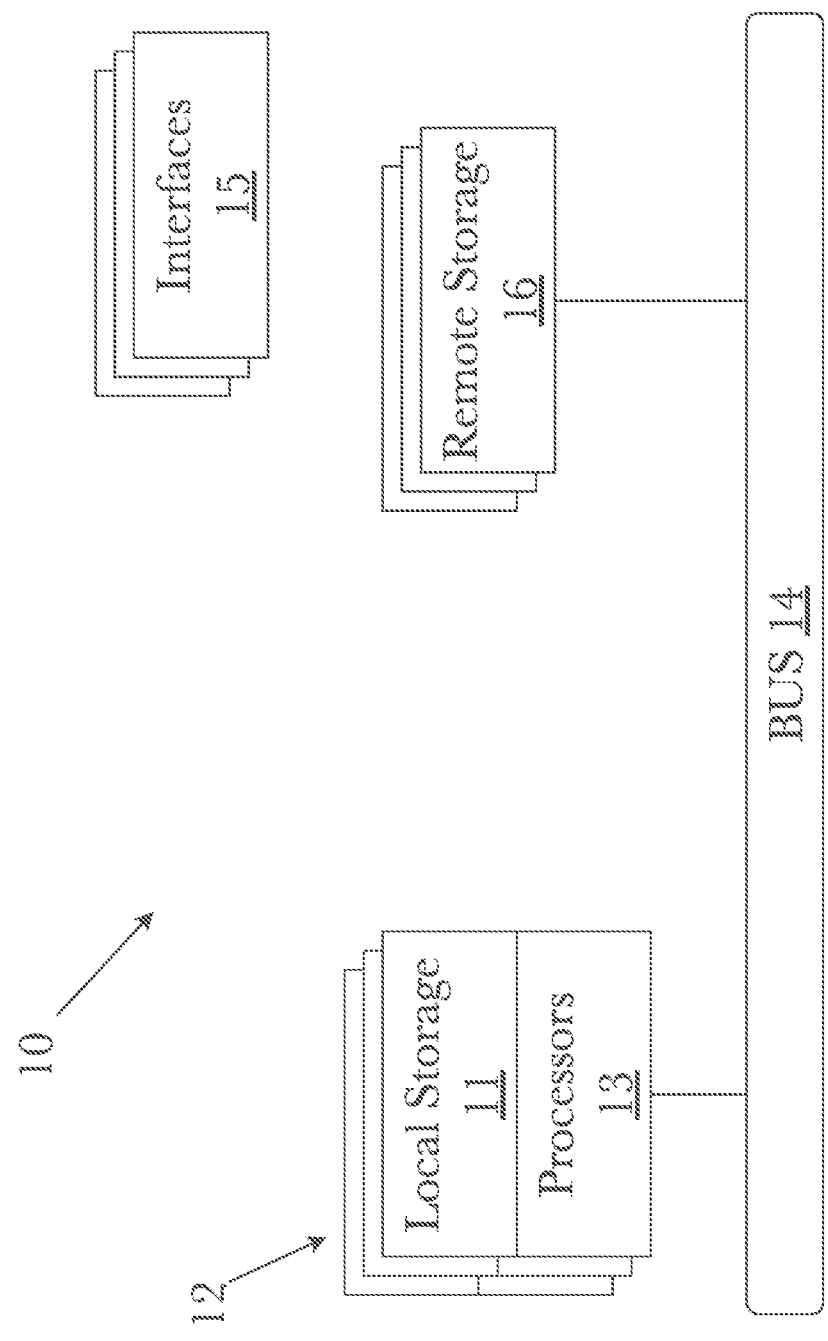
FIG. 10 is a block diagram illustrating an exemplary hardware architecture of a computing device.

Referring now to FIG. 10, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random-access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 10 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 11:
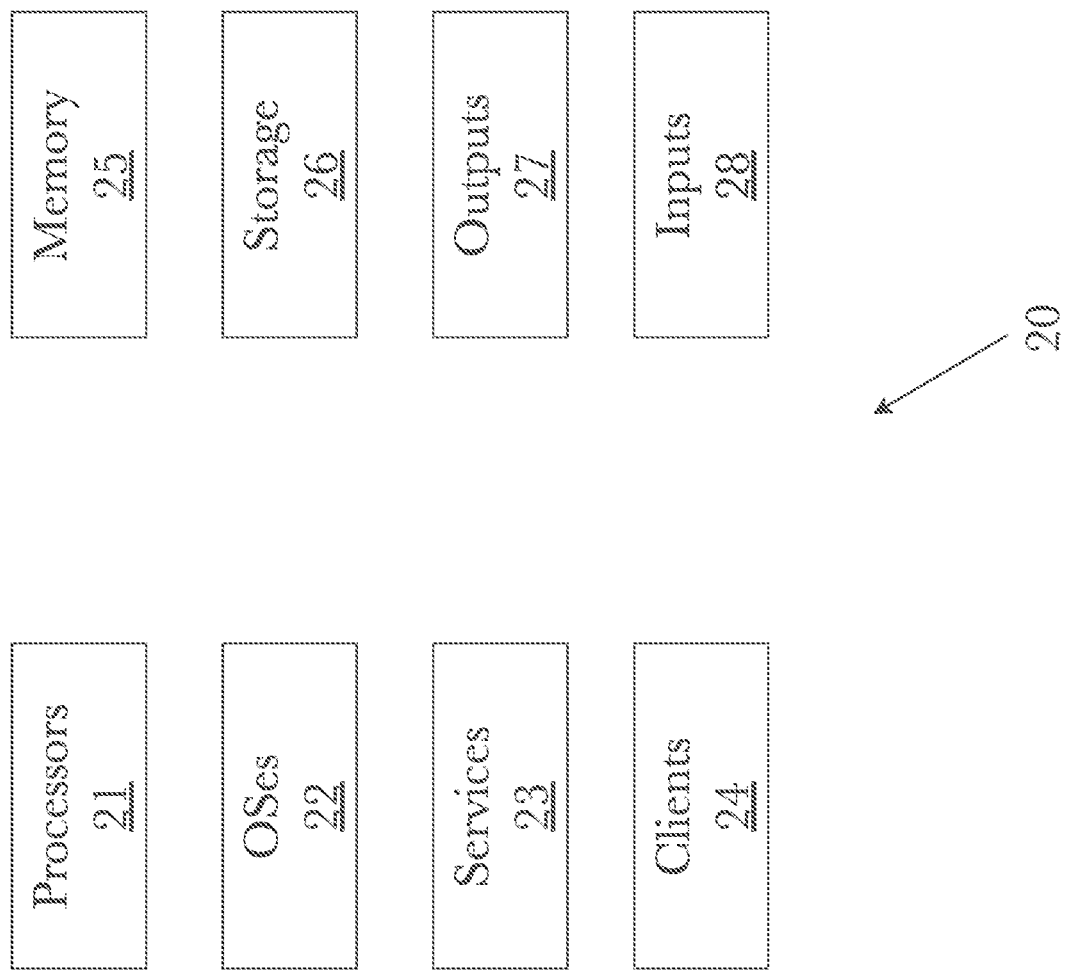
FIG. 11 is a block diagram illustrating an exemplary logical architecture for a client device.

In some aspects, systems may be implemented on a standalone computing system. Referring now to FIG. 11, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 10). Examples of storage devices 26 include flash memory, magnetic hard drive, CD-ROM, and/or the like.

Figure 12:
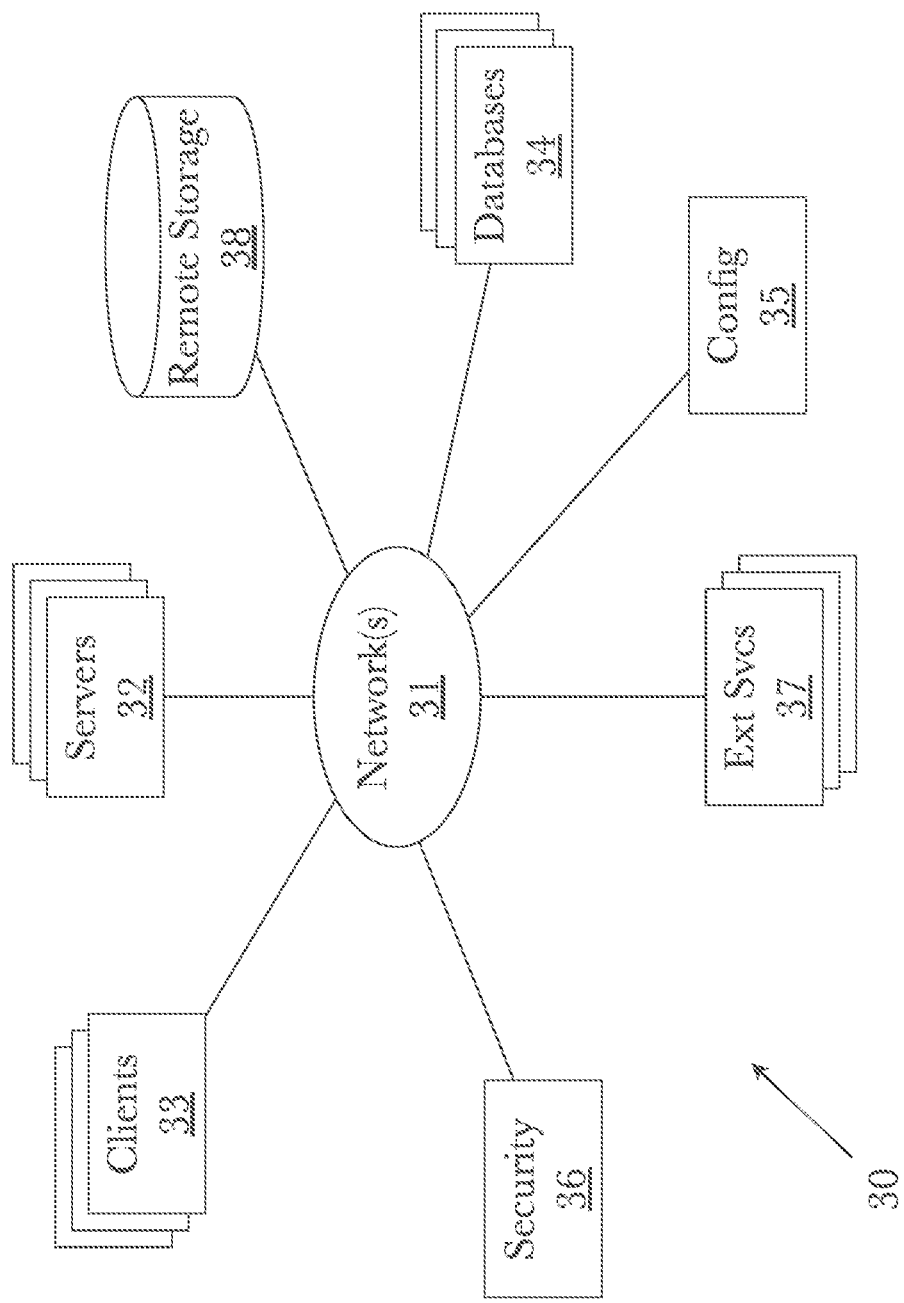
FIG. 12 is a block diagram showing an exemplary architectural arrangement of clients, servers, and external services.

In some aspects, systems may be implemented on a distributed computing network, such as one having any number of clients and/or servers. Referring now to FIG. 12, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 11. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises. In addition to local storage on servers 32, remote storage 38 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in the art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

Figure 13:
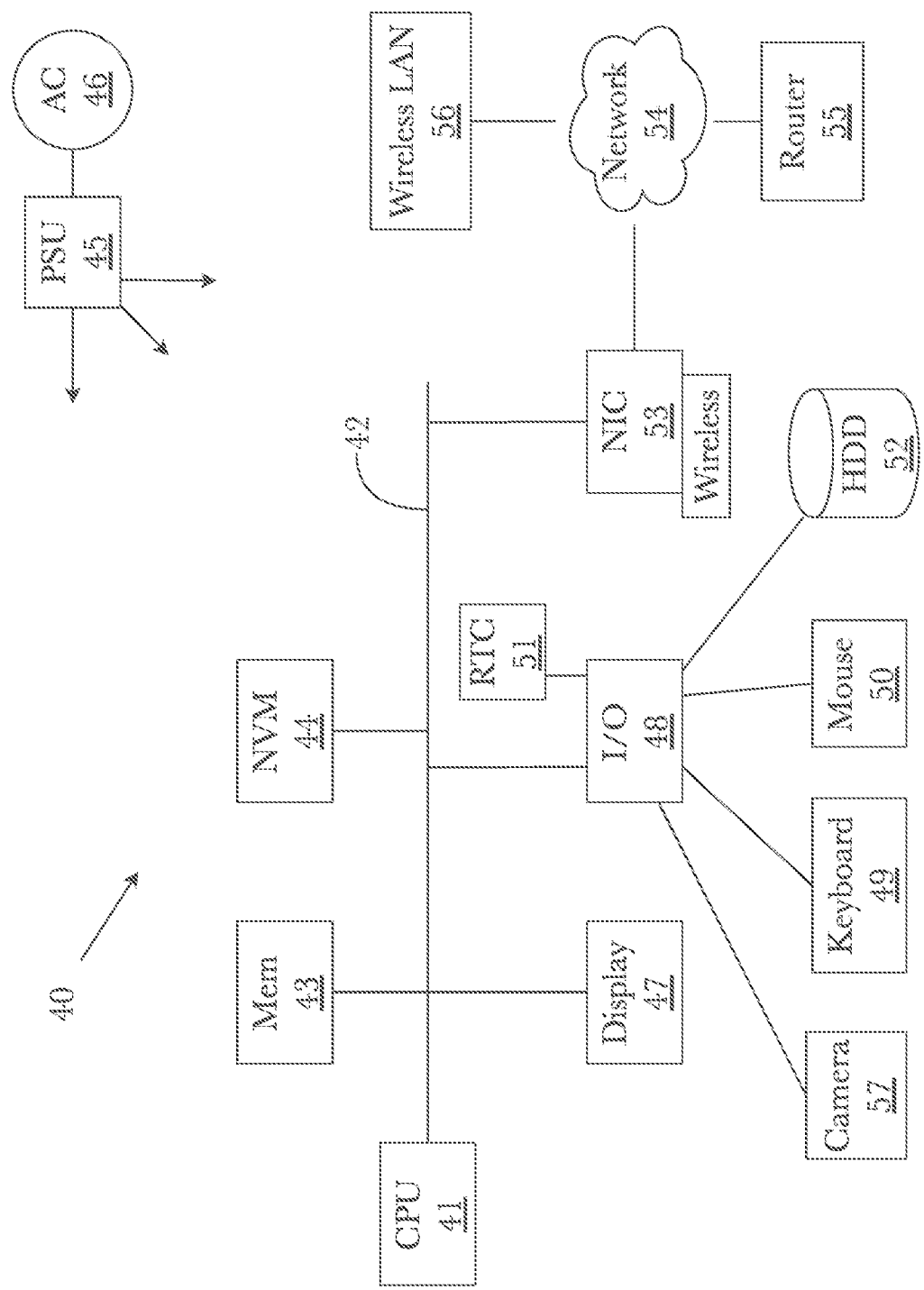
FIG. 13 is another block diagram illustrating an exemplary hardware architecture of a computing device.

FIG. 13 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router 55, wireless local area network 56, or any other network connection. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. A system for selection and distribution of dietary supplements based on genetic testing, comprising:
   a network-connected computer server comprising a memory, a processor, and a non-volatile data storage device;
   a business management database stored on the non-volatile data storage device, the business management database comprising:
      seller data comprising a seller identification for each seller and inventories of products available from each seller;
      product data comprising information about amounts of dietary supplements contained in a plurality of dietary supplement products; and
      client data comprising client names, ages, weights, and health conditions;
   a seller portal comprising a first plurality of programming instructions stored in the memory which, when operating on the processor, causes the processor to:
      receive seller data from a plurality of sellers; and
      store the seller data in the business management database on the non-volatile data storage device;
   a client portal comprising a second plurality of programming instructions stored in the memory which, when operating on the processor, causes the processor to:
      receive client data for a first client comprising the client's name, age, weight, and a health condition;
      receive a request for selection and distribution of dietary supplements that are beneficial to the health condition;
      receive a genetic profile from the client, the genetic profile comprising the results of a deoxyribonucleic acid (DNA) test for the client; and
      store the client data and genetic profile in the business management database;
   a machine learning algorithm comprising a third plurality of programming instructions stored in the memory which, when operating on the processor, causes the processor to:

receive the genetic profile;
retrieve the first client's data and genetic profile from the business management database; and
identify a dietary supplement known or suspected to be beneficial to the health condition;
determine an amount of the dietary supplement based on the client's age and weight;
an inventory manager comprising a fourth plurality of programming instructions stored in the memory which, when operating on the processor, causes the processor to:
receive the identification and amount of the dietary supplement;
identify products from the business management database containing the dietary supplement in at least the amount;
determine availability of the identified products from the inventories of the sellers in the business management database;
send a recommendation to the client through the client portal to purchase the identified products; and
distribute the identified products to the client.

2. The system of claim 1, wherein the seller data of the business management database further comprises hierarchical relationships between sellers, associations of customers with sellers, and commission information based on the hierarchical relationships, and wherein the system further comprises a compensation allocator comprising a fifth plurality of programming instructions stored in the memory which, when operating on the processor, causes the processor to:
determine a first seller with which the customer is associated from the business management database;
determine a hierarchical relationship with one or more second sellers based on the hierarchical relationships between sellers in the business management database, the hierarchical relationship comprising a degree of relationship between the first seller and each of the second sellers; and
allocate a portion of the purchase price as a commission to each of the second sellers depending on the degree of relation of each second seller to the first seller.

3. A method for selection and distribution of dietary supplements based on genetic testing, comprising the steps of:
receiving seller data from a plurality of sellers, the seller data comprising a seller identification for each seller and inventories of products available from each seller;
receiving product data comprising information about amounts of dietary supplements contained in a plurality of dietary supplement products;
receiving client data comprising client names, ages, weights, and health conditions;
storing the seller data, product data, and client data in a business management database on a non-volatile data storage device of a computing device comprising a memory, a processor, and the non-volatile data storage device;
receiving client data for a first client comprising the first client's name, age, weight, and a health condition;
receiving a request for selection and distribution of dietary supplements that are may be beneficial to the health condition;
receiving a genetic profile from the client, the genetic profile comprising the results of a deoxyribonucleic acid (DNA) test for the client; and
storing the first client's data and genetic profile in the business management database;
retrieving the first client's data and genetic profile from the business management database; and
identifying, using a machine learning algorithm operating on the computing device, a dietary supplement known or suspected to be beneficial to the health condition;
determining, using the machine learning algorithm, an amount of the dietary supplement based on the client's age and weight;
identifying, using an inventory manager operating on the computing device, products from the business management database containing the dietary supplement in at least the amount;
determining availability of the identified products from the inventories of the sellers in the business management database, using the inventory manager;
sending a recommendation to the client through a client portal operating on the computing device to purchase the identified products; and
distributing the identified products to the client.

4. The method of claim 3, wherein the seller data of the business management database further comprises hierarchical relationships between sellers, associations of customers with sellers, and commission information based on the hierarchical relationships, and further comprising the steps of:
determining, using a compensation allocator operating on the computing device, a first seller with which the customer is associated from the business management database;
determining, using the compensation allocator, a hierarchical relationship with one or more second sellers based on the hierarchical relationships between sellers in the business management database, the hierarchical relationship comprising a degree of relationship between the first seller and each of the second sellers; and
allocating, using the compensation allocator, a portion of the purchase price as a commission to each of the second sellers depending on the degree of relation of each second seller to the first seller.

* * * * *